United States Patent [19]
Sumi et al.

[11] Patent Number: 6,057,041
[45] Date of Patent: May 2, 2000

[54] POLYESTER RELEASING FILM CONTAINING A SILICONE RESIN LAYER

[75] Inventors: Hiroyuki Sumi; Toshiya Koyama, both of Sagamihara, Japan

[73] Assignee: Teijin Limited, Osaka, Japan

[21] Appl. No.: 09/091,034

[22] PCT Filed: Oct. 1, 1997

[86] PCT No.: PCT/JP97/03504

§ 371 Date: Jun. 2, 1998

§ 102(e) Date: Jun. 2, 1998

[87] PCT Pub. No.: WO98/14328

PCT Pub. Date: Apr. 9, 1998

[30] Foreign Application Priority Data

| Oct. 3, 1996 | [JP] | Japan | 8-262898 |
| Oct. 11, 1996 | [JP] | Japan | 8-269750 |
| Nov. 13, 1996 | [JP] | Japan | 8-301778 |

[51] Int. Cl.$^7$ .................................................. B32B 9/04
[52] U.S. Cl. ..................... 428/447; 428/451; 428/910; 428/40.1
[58] Field of Search .................... 428/447, 451, 428/910, 40.1

[56] References Cited

U.S. PATENT DOCUMENTS

| 3,799,919 | 3/1974 | Gibbon et al. . |
| 4,801,458 | 1/1989 | Hidaka et al. . |
| 4,990,340 | 2/1991 | Hidaka et al. . |
| 5,225,199 | 7/1993 | Hidaka et al. . |
| 5,336,210 | 8/1994 | Hidaka et al. . |
| 5,677,024 | 10/1997 | Abe et al. ............... 428/40.1 |
| 5,723,208 | 3/1998 | Suzuki et al. ............ 428/216 |
| 5,910,370 | 6/1999 | Katsura et al. .......... 428/425.5 |
| 5,932,352 | 8/1999 | Higgins ................. 428/423.1 |

FOREIGN PATENT DOCUMENTS

| 47-34447 | 11/1972 | Japan . |
| 52-40918 | 10/1977 | Japan . |
| 525302 | 2/1993 | Japan . |
| 6171026 | 6/1994 | Japan . |
| 7268115A | 10/1995 | Japan . |
| 08048004 | 2/1996 | Japan . |

*Primary Examiner*—Robert Dawson
*Assistant Examiner*—Jeffrey B. Robertson
*Attorney, Agent, or Firm*—Sughrue, Mion, Zinn, Macpeak & Seas, PLLC

[57] ABSTRACT

A releasing film (C) comprising a polyester film (A) and a cured silicone resin layer (B) formed on at least one side of the polyester film (A), characterized in that (1) the film (A) is a biaxially oriented film formed of polyethylene-2,6-naphthalenedicarboxylate and has a surface center line average roughness (Ra) of 50 nm or less and (2) the releasing film (C) has a dimensional change of 0.2% or less under a stress of 150 gf/mm$^2$ at 120° C.; and a releasing film (C) comprising a primer layer (D) having a SiO bond, between said film (A) and said cured silicone resin layer (B). The releasing film of the present invention is excellent in heat resistance, surface properties and gas barrier properties, and has small dimensional change rate.

29 Claims, No Drawings

POLYESTER RELEASING FILM CONTAINING A SILICONE RESIN LAYER

TECHNICAL FIELD

The present invention relates to a releasing film using, as a base film, a biaxially oriented film formed of polyethylene-2,6-naphthalenedicarboxylate. More specifically, the present invention relates to a carrier film that is used in molding of a resin sheet, a ceramic sheet or the like and that can impart surface properties of high precision to a surface of the molded article. The present invention further relates to a releasing film required in silicon wafer production or the like, which has excellent releasability and contains a small amount of impurities in a releasing layer and in which the transfer of the impurities contained in the base film to the surface of the releasing layer is controlled. The present invention still further relates to a releasing film (or a protective film) used for such a material requiring the prevention of a volatile component from volatilizing as a plaster containing a volatile medicinal component.

BACKGROUND ART

There have been typically used releasing films having a cured silicone resin layer formed thereon. They are used in a variety of application fields such as a carrier film used in the production of molded article or as a protective film for an adhesive layer or for a plaster, or the like. In respective fields where the conventional releasing films are now used, there have been demanded releasing films that have further improvement in properties such as releasability, dimensional stability, transfer of impurities, gas permeability or the like.

The use of the releasing films in some application fields and their properties required will be described below.

In the production of a molded article, the releasing film is used as a carrier film in molding of a resin sheet, a resin coat, a ceramic sheet or the like.

The resin sheet is molded by coating (casting) a resin solution containing, for example, vinyl chloride or the like, on a carrier film, heating the resulting carrier film to remove a solvent therefrom, and peeling off and separating the carrier film. It is used in applications such as a marking sheet.

The releasing film is used also for laminating and molding a prepreg in the production of a printed wiring base board. That is, a solution of a thermosetting resin such as a phenolic resin or an epoxy resin is coated directly on a releasing film or is impregnated into a glass fiber cloth or paper sheet laminated on the releasing film and subsequently, the resulting releasing film is heated to remove the solvent therefrom. The releasing film is then peeled off and separated to produce a prepreg.

The resin coat is produced, for example, by coating a carrier film surface with a coating solution obtained by dissolving a resin as an adhesive in a solvent and then heating the resulting carrier film to remove the solvent.

The ceramic sheet is produced as a molded article, for example, by coating a carrier film surface with a slurry obtained by dispersing a ceramic powder, a binder or the like in a solvent, heating the resulting carrier film to remove the solvent, and then peeling and removing the carrier film.

In general, out of surfaces of a resin sheet, ceramic sheet or the like, the surface from which a carrier film has been peeled off is used frequently for applications which must have surface properties of high precision. Therefore, the surface roughness of the base film used in the carrier film has a large influence on the surface roughness of the resin sheet, ceramic sheet or the like.

As a base film of the above carrier films, there are used a variety of films, particularly a biaxially oriented polyethylene terephthalate (may be abbreviated as PET hereinafter) film. The PET film usually has its surface roughened by incorporation of a filler or the like, for the improvement of its windability. Consequently, a resin sheet, a ceramic sheet and the like, which are produced by the use of a carrier film with a filler-containing PET film as a base film, has a rough surface and, when laminated in a plurality of layers, may contain gaps between the adjacent layers.

On the other hand, the releasing film is heated to remove the solvent after it is coated with a resin solution or ceramic slurry. The heating temperature is, in many cases, close to or higher than the glass transition temperature (Tg) of the base film used in the releasing film. As a result, a problem arises that thermal deformation such as dimensional change and wrinkles occurs on the releasing film and the molded resin sheet or the like has non-uniform thickness and poor surface smoothness, thereby lowering the quality of the product. It is feared that the above problem may be more manifest as the heating time is shortened and the heating temperature is raised to increase the productivity of the resin sheet or the like.

The releasing film is used also in an another application field where high releasability is required and the transfer of the impurities to the releasing layer must be considered. An example of such an application field includes; the use of the releasing film as a protective film for an adhesive film used in the back-grinding step or dicing step of silicon wafer production.

That is, the adhesive film in which a variety of adhesive layers are laminated is used to fix a wafer in the back-grinding step or dicing step of silicon wafer production.

Particularly, in the back-grinding step, the side of the wafer on which circuits are printed is fixed by the adhesive layer, then its back surface is polished, and the adhesive layer is peeled off. Therefore, even a small amount of a residual adhesive after peeling or the transfer of impurities from the protective film for the adhesive layer to the wafer surface causes problems such as a defective printed circuit or the like and lowers the yield of semiconductor chips.

In the dicing step, a silicon wafer, while being fixed by an adhesive layer, is cut into small pieces, UV irradiation or the like is then made to reduce the adhesivity of the adhesive layer, and each piece is taken out. Each of the resulting wafer pieces is transferred to the subsequent bonding step and molding step for use therein. The adhesive film is stored usually in a state that its adhesive layer surface is protected by a releasing film, and is used in the dicing step after peeling and removing the releasing film.

In recent years, the size of silicon wafer used in the molding step has become very small. Presence of even a small amount of impurities on the wafer causes, for example, wafer cracking starting from the impurities due to the poor adhesion, resulting in lowering the yield of product.

Meanwhile, as the above protective film for adhesive layer, there has been used, for example, a releasing film comprising a polyester film and a cured silicone releasing layer formed thereon. Such a releasing film, however, has a drawback in that the impurities (oligomers and a metal compound used as a polymerization catalyst) in the polyester film tend to transfer into the silicone releasing layer and deposit on the releasing layer. The impurities deposited on the releasing layer are transferred onto the adhesive layer surface of the adhesive film and are further transferred onto a silicon wafer in the back-grinding and dicing steps of silicon wafer production, whereby reduction in the yield of product in the molding step is caused. Further, presence of impurities (uncured silicone monomer or oligomers) in the cured silicone resin constituting the releasing layer of the releasing film reduces the yield as well.

A releasing film is used also in other application field, i.e. a medical treatment field. For example, a releasing film is used as a protective film for protecting the adhesive layer of a plaster and maintaining the efficacy of the medicinal component contained in the adhesive layer. In such a medical treatment field, as a plaster which scarcely causes rash and which supplies a clinically effective amount of a medicine to the diseased part, there have been known, for example, plasters using, as a constituent, a knit of finely porous hollow fiber (WO 087/00046, WO 087/04343 and WO 090/09784). A plaster is also known which is a laminate of said knit and a very thin polyester film (Japanese Patent Application Kokai (Laid-Open) 3-816044).

As the protective layer for the medicinal component-containing adhesive layer of a plaster, a releasing paper using paper as the base material has been used. This releasing paper, however, has had a drawback in that since paper is porous, the medicinal component of the plaster bleeds out or volatilizes gradually, resulting in shortening of effective period of the medicinal component. To alleviate the drawback, a polyethylene terephthalate (PET) film having a higher gas barrier property than paper is also in use as the base material for the above protective layer. However, a releasing film having higher gas barrier properties is currently desired in order to make longer the effective period of medicinal component.

PROBLEMS THAT THE INVENTION TRIES TO SOLVE

It is the first object of the present invention is, therefore, to provide a releasing film which has excellent surface properties and also has stability to heat (i.e. a small dimensional change rate to heat).

It is the second object of the present invention is to provide releasing film which has excellent releasability and does not allow the transfer of the impurities contained in the base film to the releasing layer.

It is the third object of the present invention is to provide a releasing film having excellent gas barrier properties.

It is an another object of the present invention is to provide a releasing film usable in various applications.

Other objects of the present invention will become apparent from the following description.

MEANS FOR SOLVING THE PROBLEM

The above objects of the present invention can be achieved according to the present invention by a releasing film (C) comprising:
a polyester film (A), and
a cured silicone resin layer (B) formed on at least one side of the polyester film (A), characterized in that (1) the film (A) is a biaxially oriented film formed of polyethylene-2,6-naphthalenedicarboxylate and has a surface center line average roughness (Ra) of 50 nm or less and (2) the releasing film (C) has a dimensional change of 0.2% or less under a stress of 150 gf/mm$^2$ at 120° C.

The releasing film of the present invention will be described in more detail below.

In the present invention, a biaxially oriented film formed of polyethylene-2,6-naphthalenedicarboxylate is used as a base film of the releasing film. The polyethylene-2,6-naphthalenedicarboxylate (may be abbreviated as PEN hereinafter) constituting the biaxially oriented film is a polyester containing ethylene-2,6-naphthalenedicarboxylate as the main recurring unit.

The PEN polymer of the present invention may contain a small amount (10 mole % or less, particularly 5 mole % or less) of other copolymer component(s) as long as the resistance to heat deformation of the resulting releasing film is not impaired.

Illustrative examples of the other copolymer component include aromatic dicarboxylic acids such as terephthalic acid, isophthalic acid, phthalic acid, naphthalene-2,7-dicarboxylic acid, 4,4'-diphenyldicarboxylic acid, 4,4'-diphenyl ether dicarboxylic acid or the like; aliphatic dicacboxylic acids such as oxalic acid, adipic acid or the like; oxycarboxylic acids such as p-oxybenzoic acid, p-oxyethoxybenzoic acid or the like; and glycols such as diethylene glycol, 1,3-propylene glycol, 1,4-tetramethylene glycol, 1,6-hexamethylene glycol, neopentyl glycol or the like.

The PEN polymer of the present invention may also be copolymerized with a compound having at least three functional groups as long as the properties and film formability of the PEN are not substantially impaired. Illustrative examples of such a compound includes glycerine, pentaerythritol, trimellitic acid, pyromellitic acid or the like.

Further, the PEN polymer of the present invention may also have part or all of its terminal hydroxyl groups and/or carboxyl groups blocked with a monofunctional compound such as benzoic acid, methoxypolyalkylene glycol or the like, to improve its resistance to hydrolysis.

The PEN polymer of the present invention preferably has an intrinsic viscosity of 0.5 or more, particularly of 0.6 to 1.0. The PEN polymer is particularly preferable to be a homopolymer containing only ethylene-2,6-naphthalenedicarboxylate as a recurring unit because such a PEN polymer can give a base film excellent in mechanical properties such as Young's modulus and thermal properties such as resistance to heat deformation.

The PEN polymer can be produced by a known process. It can be produced, for example, by subjecting naphthalene-2,6-dicarboxylic acid or its ester-forming derivative and ethylene glycol or its ester-forming derivative to polycondensation in the presence of a catalyst. A PEN copolymer can be produced by adding the above polymer components to copolymer components and subjecting the mixture to polycondensation, or by mixing a homopolymer of the PEN and a polyester containing copolymer components in a molten state and subjecting the resulting mixture to an ester exchange reaction.

Preferably, the PEN polymer is allowed to contain inactive fine particles having an average particle diameter of 0.01 to 20 μm, preferably 0.05 to 5 μm, particularly preferably 0.1 to 3 μm, for improving film windability.

The content of the inactive fine particles is 0.001 to 20% by weight, preferably 0.005 to 5% by weight, particularly preferably 0.01 to 3% by weight. The average particle diameter and content of the inactive fine particles are preferably and suitably determined according to the shape and particle diameter distribution of the particles and the specification of the targeted film. The inactive fine particles may be inorganic or organic. Specific examples of the fine particles preferably include inorganic fine particles such as silica., alumina, kaolin, calcium carbonate, titanium oxide, barium sulfate, carbon black or the like; and organic fine particles such as cross-linked acrylic resin, cross-linked polystyrene resin, melamine resin, cross-linked silicone resin or the like. The PEN polymer containing the inactive fine particles even in a smaller amount than the PET polymer can still have sufficient windability because the PEN polymer has a stiffer molecular chain and therefore gives a film having higher stiffness than the PET polymer.

The inactive fine particles contained in the base film of the releasing film of the present invention are particularly preferably silica fine particles typified by spherical silica fine particles and porous silica fine particles. These preferred silica fine particles will be described below.

The spherical silica fine particles have a particle diameter ratio (long diameter/short diameter) of 1.0 to 1.2 and an average particle diameter of 0.01 to 5 $\mu$m. The average particle diameter thereof is preferably 0.1 $\mu$m or more, more preferably 0.3 $\mu$m or more so as to maintain a film surface center line average roughness (Ra) within the above range. When the average particle diameter is too large, foreign matters are easily produced. Therefore, the average particle diameter is preferably 3 $\mu$m or less, more preferably 2 $\mu$m or less. The production process of the spherical silica fine particles is not particularly limited as long as the above conditions are met. The spherical silica fine particles can be produced, for example, by producing morodisperse spheres of hydrous silica ($Si(OH)_4$) by hydrolysis of ethyl orthosilicate ($Si(OC_2H_5)_4$) and subjecting the monodisperse spheres of hydrous silica to a dehydration treatment in accordance with the following reaction formulae to grow the following silica bond three-dimensionally (Nippon Kagaku Kaishi, '81, No. 9, p. 1503).

Silica Bond

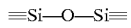

Reaction formulae

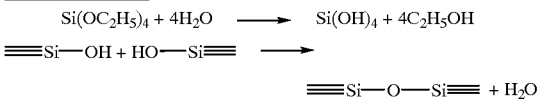

On the other hand, the porous silica fine particles are agglomerated particles.

The primary particles constituting the porous silica fine particles desirably have an average particle diameter of 0.01 to 0.1 $\mu$m. When the average particle diameter of the primary particles is smaller than 0.01 $\mu$m, ultrafine particles are produced by disintegration in the slurry stage and they form agglomerates, which is not preferred. On the other hand, when the average particle diameter of the primary particles is larger than 0.1 $\mu$m, the porosity of the particles is lost, whereby the affinity with the PEN polymer is lost and voids are liable to generate, which is not preferred. Voids decrease the transparency of the film and hence, lower its commodity value.

The porous silica fine particles preferably have a pore volume of 0.5 to 2.0 ml/g, more preferably 0.6 to 1.8 ml/g. The particles having a pore volume smaller than 0.5 ml/g are not appropriate because they have reduced porosity, whereby voids are liable to generate and transparency and light transmittance decrease. On the other hand, the particles having a pore volume larger than 2.0 ml/g are liable to have disintegration and agglomeration, whereby the control of particle diameters becomes difficult.

The average particle diameter of the porous silica fine particles is preferably 0.1 to 5 $\mu$m, more preferably 0.3 to 3 $\mu$m. When the average particle diameter is smaller than 0.1 $\mu$m, the resulting film has insufficient slipperiness. On the other hand, when the average particle diameter is larger than 5 $\mu$m, the surface of the resulting film becomes too rough and its roughness is transferred to the sheet molded on the releasing sheet, whereby the surface of the molded sheet also becomes rough. Further, the number of foreign matters in the film increases undesirably.

As mentioned above, the base film of the present invention may contain inactive fine particles. The base film, however, may also contain additives such as stabilizer, ultraviolet absorber, flame-retardant, antistatic agent or the like. Other thermosetting resin may also be contained in a small amount (for example, 20% by weight or less, particularly 10% by weight or less).

There is no restriction as to when the inactive fine particles and other additives are to be added, as long as they are added before the formation of the film from the PEN polymer. For example, they may be added in a step of polymerization or prior to the formation of the film.

The PEN film used in the present invention can be produced by any process known per se. It can be produced, for example, by drying the PEN polymer, melting the dried PEN polymer in an extruder at a temperature of Tm to (Tm+70)° C. (Tm is the melting point of the PEN polymer), extruding the molten PEN polymer from the die (e.g. T die or I die) of the extruder on-to a rotary cooling drum to quench the polymer at 40 to 90° C. to obtain an unstretched film, stretching then the unstretched film to 2.5 to 8.0 times in a longitudinal direction and to 2.5 to 8.0 times in a transverse direction at a temperature of (Tg−10) to (Tg+70)° C. (Tg is the glass transition temperature of the PEN polymer), and heat setting the stretched film at a temperature of 180 to 250° C. for 1 to 60 seconds as required. The thickness of the PEN film is preferably 1 to 250 $\mu$m, more preferably 5 to 100 $\mu$m, particularly preferably 25 to 75 $\mu$m.

The stretch ratios in the both directions are preferably almost the same so that the resulting PEN film can have good isotropy. The thus-obtained biaxially oriented and heat-set film is preferably subjected to a heat treatment at a temperature of 120 to 150° C. in a relaxed state to further improve the resistance to thermal deformation of the releasing film around 110°.

The PEN film (A) as a base film of the releasing film (C) of the present invention has a smooth surface and has a surface center line average roughness (Ra) of 50 nm or less, preferably 2 to 40 nm, particularly preferably 5 to 30 nm. When the Ra is smaller than the above range, the releasing film is liable to have blocking between films when stored in a rolled form prior before the processing step and wrinkles are liable to generate in the processing step due to the reduced slipperiness.

On the other hand, when the Ra is larger than 50 nm, the molded article using the releasing film may have a rough surface and may have voids between the releasing film and itself.

The Ra of the PEN film (A) can be maintained in the above range by controlling the average particle diameter distribution, kind and addition amount of the inactive fire particles.

The releasing film of the present invention has a cured silicone resin layer (B) formed on at least one side of the PEN film (A) as a releasing layer. The cured silicone resin layer as a releasing layer can be formed by coating the PEN film with a coating solution containing a curing silicone resin, and drying to cure the coated film.

At this time, it is possible to form a primer layer on the PEN film surface prior to the application of a coating solution containing a curable silicone resin to the film and then, apply the coating solution onto the surface of the resulting primer layer. This primer layer is described in detail later.

As the curable silicone resin, there can be used, for example, any of (1) a condensation reaction type, (2) an addition reaction type, (3) an ultraviolet or electron beam curing type, etc. They can be used singly or in combination.

The above curing reactions of the silicones can be shown as follows.

(1) Condensation reaction

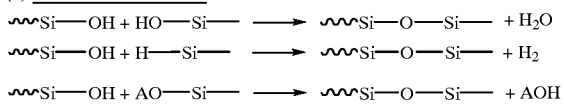

(A is a lower alkyl group.)

(2) Addition reaction

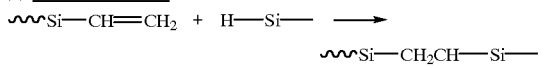

(3) Ultraviolet or electron beam curing reaction

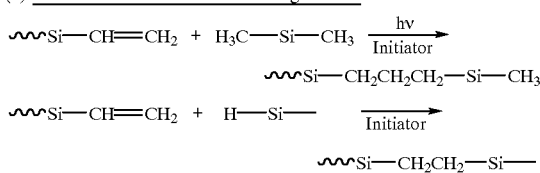

As an example of the silicone resin of condensation reaction type (1), a —OH—terminated polymethylsiloxane and a —H—terminated polydimethylsiloxane (hydrogensilane) are subjected to condensation reaction, and a three-dimensional cross-linked structure is formed by adding an organotin catalyst (e.g. an organic tin acylate catalyst) to the above condensate.

As an example of the silicone resin of addition reaction type (2), a three-dimensional structure is formed by allowing a mixture of a vinyl-terminated polydimethylsiloxane and hydrogensilane and a platinum catalyst to react each other.

As examples of the silicone resin of ultraviolet curing type (3), as the most basic types, a silicone resin is cross-linked by the same radical reaction as in ordinary silicone rubber cross-linking; a silicone resin is photo-cured after introducing an acrylic group thereinto; a silicone resin is cross-linked by a process in which an onium salt is decomposed by an ultraviolet light to generate a strong acid and the strong acid gives rise to cleavage of epoxy group; and a silicone resin is cross-linked by addition reaction of thiol to vinylsiloxane. Electron beam has a larger energy than ultraviolet light and can cause a cross-linking reaction by radical, without using any initiator like in the case of ultraviolet curing.

The curable silicone resin preferably has, a polymerization degree of about 50 to 200,000, preferably about 1,000 to 100,000. Specific examples of the curable silicone resin are KS-718, -774, -775, -778, -779H, -830, -835, -837, -838, -839, -841, -843, -847, -847H, X-62-2418, -2422, -2125, -2492, -2494, -470, -2366, -630, X-92-140, -128, KS-723A B, -705F, -708A, -883, -709 and -719, all of which are manufactured by Shin-Etsu Chemical Co., Ltd.; TPR-6701, -6702, -6703, -3704, -6705, -6722, -6721, -6700, XSR-7029, YSR-3022 and YR-3286, all of which are manufactured by Toshiba Silicone Co., Ltd.; DK-Q3-202, -203, -204, -210, -240, -3003, -205, -3057 and SFXF-2560, all of which are manufactured by Dow-Corning Corporation; SD-7226, -7320, -7229, BY24-900, -171, -312, -374, SRX-375, SYL-OFF23, SRX-244 and SEX-290, all of which are manufactured by Toray Silicone Co., Ltd.; and SILCOLEASE 425, which is manufactured by I. C. I. Japan K. K. There can also be used silicone resins disclosed in Japanese Patent Application Kokai (Laid-Open) No. 47-34447, Japanese Patent Publication No. 52-40918, etc.

In forming a cured silicone resin layer (B) on the film by the use of the curable silicone resin, a coating method conventionally known per se can be used such as bar coating, doctor blade coating, reverse roller coating, gravure coating or the like.

The drying and curing (e.g. thermal curing or ultraviolet curing) of the coating film formed must be carried out so that the resulting film has a subsequent adhesivity ratio of 85% or more, preferably 95% or more. The drying and the curing of the coating film can be carried out independently or simultaneously. When carried out simultaneously, they are preferably carried out at a temperature of 100° C. or higher. They are each carried out preferably at a temperature of 100° C. or higher for 30 seconds or longer when carried out independently. When the drying temperature is lower than 100° C. and the curing time is less than 30 seconds, undesirably, the curing of the coating film is incomplete and the coating film is liable to peel.

The thickness of the cured silicone resin layer (B) is not limited to a particular value, but is preferably 0.01 to 5 µm, particularly preferably 0.05 to 1 µm. When the thickness is smaller than 0.01 µm, the releasability of the resin layer (B) lowers and no satisfactory properties can be obtained. On the other hand, when the thickness is larger than 5 µm, a long curing time is required and is disadvantageous for production. Therefore, thickness deviated from the above range is not preferred.

The releasing film of the present invention obtained by forming a cured silicone resin layer (B) on at least one side of the PEN film (A) shows very small deformation to heat and accordingly is suitable for use under heating conditions. The deformation is expressed in terms of a dimensional change rate(%), measured under a stress of 150 gf/mm$^2$ at 120° C. according to a method described later. The dimensional change rate is measured in a stress direction and a vertical direction under conditions of the above stress and temperature, and is 0.2% or less in absolute value (i.e. −0.2% to +0.2%) in each direction. The releasing film of the present invention has a dimensional change of preferably 0.12% or less, particularly preferably 0.07% or less.

The releasing film of the present invention shows a very small dimensional change to heat as mentioned above. Therefore, it can be used advantageously as a carrier film for molding a resin sheet or a ceramic sheet.

The following releasing films (I), (II) and (III) can be given as preferred embodiments of the releasing film of the present invention. These releasing films of different constitution have respective applications for which their use is suitable. In short, the releasing film (I) comprises a PEN film (A) and a cured silicone resin layer (B) and contains no primer layer (D) therebetween. The releasing films (II) and (III) each contain a primer layer (D) between the PEN film (A) and the cured silicone resin layer (B). The releasing films (II) and (III) are basically different in the type of the primer layer (D). Each of the releasing films (I), (II) and (III) will be described below.

Releasing Film (I)

This is a releasing film (C) comprising:

a polyester film (A), and a cured silicone resin layer (B) formed on at least one side of the polyester film (A), wherein (1) the film (A) is a biaxially oriented film formed of polyethylene-2,6-naphthalenedicarboxylate and has a surface center line average roughness (Ra) of 50 nm or less, (2) the film (A) contains inorganic or organic inactive fine particles having an average particle diameter of 0.01 to 20 $\mu$m, in an amount of 0.001 to 20% by weight, and (3) the releasing film (C) has a dimensional stability of 0.2% or less under a stress of 150 gf/mm$^2$ at 120° C.

The releasing film (I) basically comprises the above PEN film (A) and the above cured silicone resin layer (B) formed on at least one side of the film (A). Therefore, the properties and production methods of the PEN film (A) and the cured silicone resin layer (B) used in the releasing film (I) are not particularly described here.

In the releasing film (I), the number of foreign matters (large coarse particles) having a size of 50 $\mu$m or more contained in the PEN film (A) as a base film is preferably 100 per/m$^2$ or less, preferably 30 per/m$^2$ or less, more preferably 10 per/n$^2$ or less. A large number of foreign matters having a size of 50 $\mu$m or more is not desirable because the resin sheet or ceramic sheet molded using the above releasing film (I) has many surface defects.

Having excellent surface properties and a small dimensional change rate, the releasing film (I) is extremely suitable as a carrier film for molding a resin sheet or a ceramic sheet.

Releasing Film (II)

This is a releasing film (C) comprising:

a polyester film (A), and a cured silicone resin layer (B) formed on at least one side of the polyester film (A), wherein (1) the film (A) is a biaxially oriented film formed of polyethylene-2,6-naphthalenedicarboxylate and has a surface center line average roughness (Ra) of 50 nm or less, (2) the releasing film (C) has a primer layer (D) having a SiO bond, between the film (A) and the cured silicone resin layer (B), and the primer layer (D) having the SiO bond is a layer formed of a condensate obtained by hydrolysis of alkoxysilane, and (3) the releasing film (C) has a dimensional stability of 0.2% or less under a stress of 150 gf/mm$^2$ at 120° C.

The releasing film (II) is characterized in that it has a primer layer (D) having a SiO bond, between the PEN film (A) and the cured silicone resin layer (B) and that the primer layer (D) is a layer formed of a condensate obtained by hydrolysis of alkoxysilane.

The primer layer (D) of the releasing film (II) can be formed by coating the surface of the PEN film (A) with an organic solvent solution of alkoxysilane, a lower alkoxysilane in particular, and heating the resulting film, for example, at a temperature of 120 to 210° C. for 10 to 60 seconds to dry and remove the solvent and simultaneously cause cross-linking and curing of the film.

The use of tetraethoxysilane (Si(OC$_2$H$_5$)$_4$) as a representative alkoxysilane is as follows. The PEN film (A) is coated with an ethanol solution of tetraethoxysilane. As the solvent (ethanol) vaporizes, tetraethoxysilane (Si(OC$_2$H$_5$)$_4$) compound comes into contact with the moisture in the air. As a result, a reaction proceeds according to the following formula to produce a compound A.

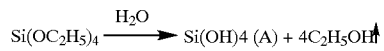

The compound (A) causes a dehydration and condensation reaction at its silanol group during its heating to dryness, whereby a uniform primer layer is formed.

The thickness of the primer layer (D) is suitably 0.02 to 2 $\mu$m. When the thickness is smaller than 0.02 $\mu$m, the effect of suppressing the transfer of the impurities contained in the PEN film (A) to the releasing layer surface is not sufficient. On the other hand, when the thickness is larger than 2 $\mu$m, the anti-blocking property of the PEN film (A) having the primer layer (D) formed thereon is poor. Therefore, thickness deviated from the above range is not preferred.

The releasing film (II) can be obtained by forming a cured silicone resin layer (B) on the thus-obtained primer layer (D) of the PEN film (A) in accordance with the above method.

In the releasing film (II), due to the presence of the above primer layer (D), the transfer of the impurities (e.g. catalyst metal component and oligomers) contained in the PEN film onto the releasing layer (the cured silicone resin layer) is suppressed considerably. Therefore, the releasing film (II) has an extremely small amount of impurities. The releasing film (II) is used very advantageously in silicon wafer production where the prevention of a very small amount of impurities from entering into the wafer is needed for management of the production process. That is, the releasing film (II) is particularly superior as a releasing film (a protective film) used in the back-grinding step and dicing step of the silicon wafer production.

Releasing Film (III)

This is a releasing film (C) comprising:

a polyester film (A), and a cured silicone resin layer (B) formed on at least one side of the polyester film (A), wherein (1) the film (A) is a biaxially oriented film formed of polyethylene-2,6-naphthalenedicarboxylate and has a surface center line average roughness (Ra) of 50 nm or less, (2) the releasing film (C) has a primer layer (D) having a SiO bond, between the film (A) and the cured silicone resin layer (B), and the primer layer (D) having a SiO bond is a SiO$_x$ (1≦x≦2) layer formed by a gas-phase deposition method, and (3) the releasing film (C) has a dimensional stability of 0.2% or less under a stress of 150 gf/mm$^2$ at 120° C.

The releasing film (III) is characterized in that it has a primer layer (D) having a SiO bond, between the PEN film (A) and the cured silicone resin layer (B) and that the primer layer (D) is a SiO$_x$ (1≦x≦2) layer formed by the gas-phase deposition method.

The primer layer (D) of the releasing film (III) is formed on the surface of the PEN film (A) as a layer of SiO$_x$ (X is within the same range as above), by the gas-phase deposition method.

Preferred examples of the gas-phase deposition method are represented by the following methods (a) to (c).

(a) A vacuum deposition method using SiO as a deposition source.

(b) A sputtering method using a SiO$_2$ substrate as a target.

(c) A plasma CVD method using an organosiloxane as a starting material.

Of these, the vacuum deposition method using SiO as a deposition source is preferred in view of cost.

The above methods can be used alone or in combination to form a SiO$_x$ layer.

The thickness of the SiO$_x$ layer is preferably 0.04 to 0.1 μm, more preferably 0.05 to 0.08 μm. When the thickness is smaller than 0.04 μm, no satisfactory gas barrier properties are obtained. On the other hand, when the thickness is larger than 0.1 μm, the SiO$_x$ layer has higher rigidity and is liable to be peeled off from the PEN layer (A) when the releasing film (III) is bent. Therefore, thickness deviated from the above range is not preferred.

The releasing film (III) can be obtained by forming a cured silicone resin layer (B) on the thus-obtained primer layer (D) of the PEN film (A) in accordance with the above method.

Since the releasing film (III) has the primer layer (D) formed thereon by the gas-phase deposition method, it has an extremely high gas barrier properties. Therefore, the releasing film (III) is particularly suitable as a releasing film (a protective film) used in applications requiring such a gas barrier properties. The releasing film (III) can be used, for example, as a protective film for the adhesive layer of a plaster containing a volatile medicinal component and can prevent the vaporization and volatilization of the medicinal component, whereby the efficacy of the plaster can be protected over a long period of time.

In the releasing films (II) and (III), a primer layer (D) having a SiO bond is formed between the PEN film (A) and the cured silicone resin layer (B). This primer layer (D) may be formed by a treatment with a silane coupling agent. The silane coupling agent represented by the general formula Y—Si—X$_3$ is particularly preferable. In the above formula, Y is a functional group represented by, for example, an amino group, an epoxy group, a vinyl group, a methacrylic group, a mercapto croup or the like, and X is a hydrolyzable functional group represented by an alkoxy group. The thickness of the primer layer formed by the treatment with a silane coupling agent is preferably 0.01 to 5 μm, more preferably 0.02 to 2 μm. When the thickness of the primer layer is in the above range, the adhesion between the base film and the releasing layer is good, and the base film having the primer layer formed thereon has a lower blocking tendency. Therefore, the releasing film obtained above is easy to handle, which is advantageous.

The releasing films of the present invention can be used not only in the above applications but also in the production of printed wiring boards used in the fields of electronic computers, communication equipment, measuring instruments, medical equipment and so on. With the recent trend of reducing the size of the circuits, multi-layer printed wiring base boards are used in these applications, and the releasing films of the present invention can be used advantageously to laminate prepregs used in the production of multi-layer printed wiring boards.

EXAMPLES

The following examples will be given to further describe the present invention. Characteristic properties in the examples were measured in accordance with the following methods.

(1) Intrinsic Viscosity of PEN Polymer

The intrinsic viscosity of a PEN polymer was measured at 35° C. in o-chlorophenol.

(2) Surface Center Line Average Roughness (Ra)

The film surface was scanned using a needle-contacting type surface roughness tester (Surfcorder 30C, manufactured by Kosaka Kenkyusho K. K.) under the condition of a needle radius of 2 μm and needle pressure of 30 mg to measure the displacement of the film surface, thereby drawing a surface roughness curve. From the surface roughness curve, a length (L) measured in the direction of its center line was extracted, and when the surface roughness curve was expressed as (Y=f(x)) for which a scanning length was taken as X axis and the surface displacement was taken as Y axis, the surface center line average roughness (Ra) of the film was calculated using the following formula:

$$Ra = \frac{1}{L}\int_0^L |f(x)| dx$$

(3) Dimensional Change Rate

A rectangular film having a length of 30 mm or more in a longitudinal direction and 4 mm in a transverse direction was prepared and fitted to the zig of a TMA (TMA/SS120C, a thermal stress-strain tester, manufactured by Seiko Instruments Inc.) so that the distance between chucks became 10 mm. The film was heated from a room temperature at a temperature elevation rate of 5° C. /min under application of a stress of 150 gf/mm. The film was measured for dimensional changes in a stress direction and in a vertical direction at the time when the film temperature reached 120° C., respectively. The dimensional change rate of the film was determined using the following formula.

Dimensional change rate (in absolute value)=(dimensional change/distance between chucks)×100

(4) Analysis of Metal Element on a Cured Silicone Resin Layer (Releasing Layer) Surface A polyester adhesive tape (Nitto 31B, manufactured by Nitto Denko Corporation) was stuck on the releasing layer of a releasing film, contact-bonded by the use of a pressure roll at a pressure of 5 kg/cm$^2$ and allowed to stand at 70° C. for 20 hours. Thereafter, the adhesive tape was peeled off from the releasing film and metal elements on the peeled surface of the adhesive tape were analyzed by the use of an ESCA apparatus, using MgKα (1,254 eV) as an excitation source, to examine the metal elements which were transferred from the releasing film to the adhesive tape. In the measurement of metal elements by ESCA, a metal element was regarded as being present in the layer when a metal element having peaks exceeding 50 counts was detected.

(5) Measurement of Oligomers

A releasing film was heated in an oven at 180° C. for 5 minutes, taken out, and cooled. Thereafter, the releasing layer of the releasing film was subjected to sputtering with Au, and 10 sites, having an area of 10 μm$^2$ each, on the layer were observed through a scanning electron microscope at a magnification of 2,000×. A case where no crystals (hexagonal prism-shaped crystals) of oligomers were observed in any of the 10 sites was regarded as no presence of oligomers on the releasing layer of the releasing film.

(6) Subsequent Adhesivity Ratio

A polyester adhesive tape (Nitto 31B) was stuck on a cold rolled stainless steel plate (SUS 304) specified in accordance with JIS G4305 to measure peeling strength. This peeling strength was taken as basic adhesivity (f$_o$). The above polyester adhesive tape was stuck on the releasing layer of a sample film. The resulting sample film was subjected to contact-bonding by the use of a pressure roll at a pressure of 5 kg and allowed to stand for 30 seconds, and the adhesive tape was then peeled off. This peeled adhesive tape was stuck on the above stainless steel plate, and the stuck portion was measured for peeling strength. This peeling strength was taken as subsequent adhesivity (E). A subsequent adhesivity ratio (%) was determined from the basic adhesivity (f$_o$) and the subsequent adhesivity (f), using the following formula.

Subsequent adhesivity ratio(%)=(f/f$_o$)×100

(7) Peeling Strength

A polyester adhesive tape (Nitto 31B) was stuck on the releasing layer of a releasing film. The resulting film was subjected to contact-bonding by the use of a pressure roll at a pressure of 5 kg and allowed to stand for 20 hours. Then, the peeling strength (R$_{fo}$) between the releasing layer and the adhesive tape was measured by the use of a tensile tester.

(8) Oxygen Gas Permeability

The permeability of an oxygen (80)/carbon dioxide (20) mixed gas through a film was measured by a gas chromatography method at 25° C. using a gas permeability coefficient tester, manufactured by Lyssy Co., Ltd. of Switzerland.

(9) Volatilization of Medicinal Component

An acrylic adhesive containing 2% by weight of progesterone as a medicinal component was coated on the releasing layer of a releasing film so that the film has a thickness of 15 μm when dried. The resulting film was dried at 70° C. for 3 minutes to form an adhesive layer containing a medicinal component. On the adhesive layer was contact-bonded the same releasing film, and the resulting film was allowed to stand in a flow of air at 37° C. for 7 days. Thereafter, the releasing film was peeled off and the resultant condition of the adhesive layer containing a medicinal component was compared with its initial condition and the change therebetween was observed visually. The change was evaluated based on the following evaluation criterion.

○: No change

X: Changed (the adhesive layer cured, the medicinal component volatilized, etc.)

(10) Processability

The frequency of various troubles occurring in the production of a releasing film was collectively evaluated based on the following criterion. The troubles included occurrence of meandering caused by sagging, poor surface smoothness or the like; occurrence of wrinkles formed due to liability to form wrinkles at a nip roll during winding, slipperiness, surface smoothness or the like; occurrence of defects of applied coating; and so forth.

◎: Substantially no troubles occurs during the process.

○: Troubles occur during the process occasionally but at a low frequency.

Δ: Troubles occur during the process occasionally.

x: Troubles occur during the process at a high frequency.

(11) Percentage of Defective Product

A releasing film produced was evaluated for occurrence of pimples and unevenness in a rolled form and for occurrence of adhesion between films, defects of applied coating, surface defects, surface flatness, presence of foreign matters (e.g. bubbles), sagging or the like, in an unrolled form. Based on the evaluation, the percentage of the number of releasing film rolls unsuitable as a product to the number of total releasing film rolls was calculated and taken as a percentage of defective product.

Example 1

A PEN polymer having an intrinsic viscosity of 0.62 was melted in an extruder. The molten polymer was extruded from the die of the extruder onto a rotary cooling drum kept at 40° C., and was electrostatically close-contacted therewith and quenched to obtain an unstretched film. The unstretched film was stretched to 3.7 times in a longitudinal direction and to 3.8 times in a transverse direction, and heat set at 240° C. to obtain a biaxially oriented PEN film having a thickness of 50 μm.

On one side of the biaxially oriented PEN film was coated the following coating solution in an amount of 6 g/m$^2$ (wet), and the coated surface was dried and cured at 140° C. for 1 minute to produce a releasing film having a releasing layer of 0.15 μm in thickness. The coating solution was prepared by dissolving a curing silicone of addition-reaction type comprising a vinyl group-containing polydimethylsiloxane and dimethylhydrogensilane, in a mixed solvent of methyl ethyl ketone, methyl isobutyl ketone and toluene, adding a silicone resin thereto so as to become an amount of 10% by weight based on the solid content of the curing silicone to obtain a solution having the total solid content of 2%, and adding a platinum catalyst to the resulting solution. The properties of the obtained releasing film are shown in Table 1.

TABLE 1

|  | Surface roughness (nm) | Dimensional change (in absolute value) | |
| --- | --- | --- | --- |
|  |  | Stress direction (%) | Vertical direction (%) |
| Example 1 | 6 | 0.06 | 0.06 |

As is clear from Table 1, the releasing film in Example 1 of the present invention has small surface roughness and excellent dimensional change rate.

Examples 2 to 5 and Comparative Examples 2 to 3

Dimethyl naphthalene-2,6-dicarboxylate and ethylene glycol were subjected to an ester interchange reaction in the presence of manganese acetate in accordance with a commonly used method, and trimethyl phosphate was then added thereto. Thereafter, antimony trioxide and inactive fine particles having an average particle diameter shown in Table 2 were added to the resulting product in the amounts shown in Table 2. The resulting mixture was subjected to polycondensation in accordance with a commonly used method to obtain polyethylene-2,6-naphthalate polymers having an intrinsic viscosity of 0.62. The obtained polymers were dried at 170° C. for 6 hours, fed into an extruder, melted at a temperature of 290° C. to 310° C., and then extruded from the slit die of the extruder having a slit of 1.5 mm onto a rotary drum having a surface finish of 0.3S and a surface temperature of 50° C., to obtain unstretched films.

The unstretched films were stretched to 3.6 times at 140° C. in a longitudinal direction and to 3.7 times at 150° C. in a transverse direction, and heat set at 240° C. to obtain biaxially oriented PEN films having a thickness of 50 μm.

On one side of the biaxially oriented PEN films was coated the following coating solution in an amount of 6 g/m$^2$ (wet), and the coated surface was dried and cured at 140° C. for 1 minute to produce releasing films having a releasing layer of 0.15 μm in thickness. The coating solution was prepared by dissolving a curing silicone of addition-reaction type comprising a vinyl group-containing polydimethylsiloxane and dimethylhydrogensilane in a mixed solvent of methyl ethyl ketone, methyl isobutyl ketone and toluene, adding a silicone resin so as to become an amount of 10% by weight based on the solid content of the curing silicone to obtain a solution having a total solid content of 2%, and adding a platinum catalyst to the resulting solution. The properties of the obtained releasing films are shown in Table 2.

Comparative Example 1

A PET polymer obtained by a commonly used method, which contained inactive fine particles shown in Table 2 and has an intrinsic viscosity of 0.62, was melted in an extruder. The molten polymer was extruded from the die of the extruder onto a rotary cooling drum kept at 40° C., electrostatically close-contacted therewith, and quenched to obtain an unstretched film. The unstretched film was stretched 3.6 times in a longitudinal direction and to 3.9 times in a transverse direction, and heat set at 220° C. to obtain a biaxially oriented PET film having a thickness of 50 μm.

On one side of the biaxially oriented PET film was coated the following coating solution in an amount of 6 g/m² (wet), and the coated surface was dried and cured at 140° C. for 1 minute to produce a releasing film having a releasing layer of 0.15 μm in thickness. The coating solution was prepared by dissolving a curing silicone of addition-reaction type comprising a vinyl group-containing polydimethylsiloxane and dimethylhydrogensilane in a mixed solvent of methyl ethyl ketone, methyl isobutyl ketone and toluene to obtain a solution having the total solid content of 2%, and adding a platinum catalyst to the resulting solution. The properties of the obtained releasing film are shown in Table 2.

composition in an amount (wet) of 8 g/m². The coated portion of the layer was dried and cured at 130° C. for 30 seconds to obtain a releasing film having a releasing layer of 0.24 μm in thickness. The properties of the obtained releasing film are shown in Table 3.

| <Composition of silicone resin coating solution> | |
| --- | --- |
| Curable silicone resin (KS847H, a product of Shin-Etsu Chemical Co., Ltd.) | 100 parts by weight |
| Catalyst (CAT PL-50T, a product of Shin-Etsu Chemical Co., Ltd.) | 2 parts by weight |
| Diluent: methyl ethyl ketone/xylene/methyl isobutyl ketone mixed solvent | 898 parts by weight |

Comparative Example 4

A releasing film was produced in the same manner as in Example 6 except that the polyethylene-2,6-naphthalate used in Example 6 was replaced by polyethylene terephtha-

TABLE 2

| | Example 2 | Comparative Example 1 | Example 3 | Example 4 | Example 5 | Comparative Example 2 | Comparative Example 3 |
| --- | --- | --- | --- | --- | --- | --- | --- |
| Base material | PEN | PET | PEN | PEN | PEN | PEN | PEN |
| Lubricant | Spherical silica | Spherical silica | Porous silica particles | Porous silica particles | Porous silica particles | Porous silica particles | Porous silica particles |
| Amount added (%) | 0.10 | 0.10 | 0.006 | 0.015 | 0.08 | 0.2 | 0.08 |
| Average particle diameter (μm) | 0.35 | 0.35 | 1.3 | 1.3 | 1.3 | 1.3 | 3.1 |
| Particle diameter ratio | 1.08 | 1.08 | — | — | — | — | — |
| Agglomeration degree of primary particles | — | — | 0.02 | 0.02 | 0.02 | 0.02 | 0.11 |
| Pore volume (ml/g) | — | — | 1.5 | 1.5 | 1.5 | 1.5 | 2.2 |
| Stretch ratio | | | | | | | |
| Longitudinal direction | 3.6 | 3.6 | 3.6 | 3.6 | 3.6 | 3.6 | 3.6 |
| Transverse direction | 3.7 | 3.9 | 3.7 | 3.7 | 3.7 | 3.7 | 3.7 |
| Surface roughness Ra (nm) | 6 | 6 | 8 | 16 | 36 | 60 | 65 |
| Number of foreign matters (per/m²) | 2 | 3 | 2 | 5 | 12 | 28 | 110 |
| Dimensional change rate | | | | | | | |
| Longitudinal direction (%) | 0.06 | 0.5 | 0.06 | 0.06 | 0.06 | 0.06 | 0.06 |
| Transverse direction (%) | 0.06 | 0.4 | 0.06 | 0.06 | 0.06 | 0.06 | 0.06 |
| percentage of defective product (%) | 3 | 28 | 2 | 6 | 13 | 32 | 46 |
| Processability | ○ | X | ○ | ○ | ◉ | ◉ | X |

Example 6

Polyethylene-2,6-naphthalate having an intrinsic viscosity of 0.62, obtained by polymerization using an antimony compound and a manganese compound as the catalyst, was melted in an extruder. The molten polymer was extruded from the die of the extruder onto a rotary cooling drum kept at about 40° C. to form a film, and the film was electrostatically close-contacted on the drum and quenched to obtain an unstretched film. The unstretched film was stretched to 3.7 times in a longitudinal direction and to 3.8 times in a transverse direction, and heat set at 240° C. to obtain a biaxially oriented film having a thickness of 50 μm. Onto this film was coated with an isopropyl alcohol solution of $Si(OC_2H_5)_4$ (Colcoat P, manufactured by Colcoat Co., Ltd.) by a gravure coating method. The coated surface thereof was dried and cured at 140° C. for 30 seconds to form an anchor coat layer having a thickness of 0.5 μm.

On the anchor coat layer of the biaxially oriented film was coated a silicone resin coating solution having the following late (having an intrinsic viscosity, measured in o-chlorophenol at 25° C., of 0.65) obtained by polymerization of dimethyl terephthalate and ethylene glycol in the presence of an antimony compound and a manganese compound as catalysts. The properties of the obtained releasing film are shown in Table 3.

Comparative Example 5

A releasing film was produced in the same manner as in Example 6 except that no anchor coat layer was formed on the polyethylene-2,6-naphthalate film and, instead, a corona treatment was applied onto the film so that the wetting index of the corona-treated surface of the film became 50 dyn/cm and that the silicone resin coating solution was coated on the corona-treated surface. The properties of the obtained releasing film are shown in Table 3.

Comparative Example 6

A releasing film was produced in the same manner as in Example 6 except that the amount of the catalyst in the silicone resin coating solution was reduced to 0.5 part by weight. The properties of the obtained releasing film are shown in Table 3.

TABLE 3

| | Metal elements on releasing layer | Oligomers | Subsequent adhesivity ratio % | Peeling strength g/in |
|---|---|---|---|---|
| Example 6 | Not present | Not present | 98 | 3 |
| Comparative Example 4 | Mn, Sb | Present | 98 | 5 |
| Comparative Example 5 | Not present | Present | 97 | 4 |
| Comparative Example 6 | Not present | Not present | 83 | 7 |

Example 7

One side of the biaxially oriented PEN film having a thickness of 50 μm, obtained in Example 2, was vapor-deposited with SiO by high frequency induction heating to form a $SiO_x$ layer thereon. The thickness of the layer was measured using a quarts oscillator and was 70 nm. The resulting material was kept at 23° C. for 24 hours to stabilize the $SiO_x$ layer.

The $SiO_x$ layer was coated with a silicone resin coating solution in an amount (wet) of 8 g/m². The silicone resin coating solution was obtained by dissolving a curable silicone (KS-847 (H), manufactured by Shin-Etsu Chemical Co., Ltd.), of an addition reaction type comprising a mixture of polydimethylsiloxane and dimethylhydrogensilane and a platinum catalyst, in a methyl ethyl ketone/methyl isobutyl ketone/toluene mixed solvent. The coated $SiO_x$ layer was dried and cured at 130° C. for 30 seconds to obtain a releasing film having a releasing layer of 0.24 μm in thickness. The properties of the obtained releasing film are shown in Table 4.

Comparative Example 7

A releasing film was produced in the same manner as in Example 7 except that the thickness of the $SiO_x$ layer was changed to 120 nm. The properties of the obtained releasing film are shown in Table 4.

TABLE 4

| | Peeling strength g/in | Subsequent adhesivity ratio % | Oxygen gas permeability cc · cm/(cm² · sec · mmHg) | Volatilization of medicinal component |
|---|---|---|---|---|
| Example 7 | 3 | 89 | $8.0 \times 10^{-15}$ | ○ |
| Comparative Example 7 | (Note) | (Note) | (Note) | x |

(Note): The deposition layer was peeled off at the time of applying a silicone resin coating solution and no releasing film was obtained.

What is claimed is:

1. A releasing film (C), comprising
   a polyester film (A), and
   a cured silicone resin layer (B) formed on at least one side of a polyester film (A),
   characterized in that (1) the film (A) is a biaxially oriented film formed of polyethylene-2,6-naphthalenedicarboxylate and has a surface center line average roughness (Ra) of 50 nm or less, (2) the releasing film (C) has a dimensional change rate of 0.2% or less under stress of 150 gf/mm² at 120° C. and (3) the releasing film (C) comprises a primer layer (D) having a SiO bond between the film (A) and the cured silicone resin layer (B).

2. The releasing film of claim 1, which has a subsequent adhesivity ratio of 85% or more.

3. The releasing film of claim 1, wherein the film (A) has a thickness of 1 to 250 Ξm.

4. The releasing film of claim 1, wherein the silicone resin layer (B) has a thickness of 0.01 to 5 μm.

5. The releasing film of claim 1, wherein the film (A) has a surface center line average roughness (Ra) of 10 nm or less.

6. The releasing film of claim 1, wherein the primer layer (D) has a thickness of 0.04 to 2 μm.

7. The releasing film of claim 1, wherein the primer layer (D) is a $SiO_x$ ($1 \leq x \leq 2$) layer having a thickness of 40 to 100 μm, formed by a gas-phase deposition method.

8. The releasing film of claim 1, wherein the primer layer (D) is formed by a treatment with a silane coupling agent.

9. The releasing film of claim 1, wherein the film (A) contains inactive fine particles in an amount of 0.001 to 20% by weight.

10. The releasing film of claim 1, wherein the inactive fine particles have an average particle diameter of 0.01 to 20 μm.

11. A releasing film (C) comprising:
    a polyester film (A), and
    a cured silicone resin layer (B) formed on at least one side of the polyester film (A),
    characterized in that (1) the film (A) is a biaxially oriented film formed of polyethylene-2,6-naphthalenedicarboxylate and has a surface center line average roughness (Ra) of 50 nm or less, (2) the releasing film (C) has a primer layer (D) having a SiO bond, between the film (A) and the cured silicone resin layer (B), and the primer layer (D) having a SiO bond is a layer formed of a condensate obtained by hydrolysis of alkoxysilane, and (3) the releasing film (C) has a dimensional stability of 0.2% or less under a stress of 150 gf /mm² at 120° C.

12. The releasing film of claim 11, wherein the subsequent adhesivity ratio of the surface of the cured silicone resin layer (B) is 85% or more.

13. The releasing film of claim 11, wherein the primer layer (D) has a thickness of 0.02 to 2 μm.

14. The releasing film of claim 11, wherein the primer layer (D) is a layer formed of a condensate obtained by hydrolysis of tetraethoxysilane.

15. The releasing film of claim 11, wherein the film (A) has a thickness of 1 to 250 μm.

16. The releasing film of claim 11, wherein the cured silicone resin layer (B) has a thickness of 0.01 to 5 μm.

17. A releasing film (C) comprising:
    a polyester film (A), and
    a cured silicone resin layer (B) formed on at least one side of the polyester film (A),
    characterized in that (1) the film (A) is a biaxially oriented film formed of polyethylene-2,6-naphthalenedicarboxylate and has a surface center line average roughness (Ra) of 50 nm or less, (2) the releasing film (C) has a primer layer (D) having a SiO bond, between the film (A) and the cured silicone resin layer (B), and the primer layer (D) having a SiO bond is a $SiO_x$ ($1 \leq x \leq 2$) layer formed by a gas-phase deposition method, and (3) the releasing film (C) has a dimensional stability of 0.2% or less under a stress of 150 gf/ m² at 120° C.

18. The releasing film of claim 17, wherein the primer layer has a thickness of 0.02 to 0.1 μm.

19. The releasing film of claim 17, wherein the gas-phase deposition method is a vacuum deposition method, a sputtering method or a plasma CVD method.

20. The releasing film of claim 23, wherein the film (A) has a thickness of 1 to 250 μm.

21. The releasing film of claim 17, wherein the cured silicone resin layer (B) has a thickness of 0.01 to 5 μm.

22. The releasing film of claim 17, which has an oxygen gas permeability of $1 \times 10^{-14}$ cc.cm/(cm$^2$.sec.mmHg) or less.

23. The releasing film of claim 1 or claim 11, which is used in the back-grinding step or dicing step of silicon wafer production.

24. The releasing film of claim 1 or claim 17, which is used for a plaster containing a volatile medicinal component.

25. The releasing film of claim 1 or claim 17, which is used as a carrier film in molding of a resin sheet or a ceramic sheet.

26. A method for producing a silicon wafer, wherein the releasing film of claim 1 or claim 11 is used as a protective film for an adhesive film used to fix the silicon wafer in a back-grinding step or a dicing step of silicon wafer production.

27. A method for preventing from volatilizing a medical component from a plaster, wherein the releasing film of claim 1 or claim 17 is used as a protective film for an adhesive plaster.

28. A method for molding a resin sheet, wherein the releasing film of claim 1 or claim is used a carrier film which is coated with a resin solution.

29. A method for molding a ceramic sheet, wherein the releasing film of claim 1 or claim 11 is used as a carrier film which is coated with a slurry.

* * * * *